United States Patent [19]

Jones

[11] 4,175,339

[45] Nov. 27, 1979

[54] DIAGNOSTIC SKILLS TEST

[76] Inventor: S. E. Jones, 7120 Birchwood Dr., Dallas, Tex. 75240

[21] Appl. No.: 856,630

[22] Filed: Dec. 27, 1977

[51] Int. Cl.² .............................................. G09B 3/02
[52] U.S. Cl. ................................................... 35/48 A
[58] Field of Search ....................................... 35/48 A

[56] References Cited

U.S. PATENT DOCUMENTS

| | | | |
|---|---|---|---|
| 1,705,657 | 3/1929 | Clapp et al. | 35/48 A |
| 2,614,338 | 10/1952 | Clark | 35/48 A |
| 2,788,590 | 4/1957 | Ormsby | 35/48 A |
| 2,977,689 | 4/1961 | Rugland et al. | 35/48 A |
| 3,280,483 | 10/1966 | Davenport | 35/48 A |
| 3,693,267 | 9/1972 | Bertolet | 35/48 A |

*Primary Examiner*—William H. Grieb
*Attorney, Agent, or Firm*—Hubbard, Thurman, Turner, Tucker & Glaser

[57] ABSTRACT

A diagonostic test for students which has physical structure facilitating the grading thereof and which contains means for prescribing additional study materials for remediation.

4 Claims, 2 Drawing Figures

DIAGNOSTIC SKILLS TEST

BACKGROUND OF THE INVENTION

1. Field of the Invention

The present invention relates to written diagnostic tests and more particularly to a written diagnostic test whose physical structure permits the answers to interrogatories to be placed on the test near the space where the student's answers are to be recorded, without being visible to the student, and which contemplates the use of a series of written prescriptions whereby the grader may indicate any of a choice of references for remediation appropriate to the needs and ability of the student.

2. Discussion of the Prior Art

The written examination has long been used as a testing and instructional device in education. In response to interrogatories on a typical written examination, a student records an answer on paper, which is sometimes provided with special lines, boxes or other notation to indicate a place for the answer. In correcting a simple and short examination, a grader may rely upon his or her memory to supply the correct response to a question which is then compared with the student's response to measure the student's performance. An examination of greater length or complexity, however, may require a grader to use a "key", extraneous sheets of paper upon which are recorded the answers to the interrogatories. Use of a key requires a grader to physically look to the key for the correct response, then look to the student's paper to compare the response which the student has recorded. Use of a key is not only time consumming and fatiquing for the grader, but it introduces errors caused by the inadvertent comparison of the correct answer of one question with the student's response to another.

More reliable and more efficient methods of grading examinations are obviously known to the art. One method is the use of a multiple choice examination wherein the student supplies an answer in a specific location on the test paper. The test may then be graded by placing a punctuated sheet over the students answer sheet in which apertures in the sheet correspond to the locations on the student's answer sheet where the correct answer should appear. The disadvantage of using punctuated answer sheets is that they only facilitate the grading of various objective type examinations, such as those requiring multiple choice or true-false answers, and not other modes of examination, such as those requiring short written answers.

Examinations may also be mechanically graded. While mechanical grading is extremely reliable because it eliminates human error and is theoretically faster, in practice it is impractical because it is expensive and the grading means are not easily accessible for the ordinary classroom teacher. Mechanical grading usually requires that the examinations be collected and sent to a distant location for grading. Frequently, the time required for shipping, grading and returning examinations is much greater than the time that would be required if the instructor personally scored the examination. In any event, machine grading is only possible for multiple choice responses eliminating other modes of examination such as short answer and fill-in-the-blank type questions.

Similar in some respects to the present invention is a physical structure used by the Nelson-Denny Reading Test, published by Houghton Mifflin Company. This prior-art test consists of an examination booklet and an answer sheet. The answer sheet comprises two sheets of paper bonded together at the margins, the top surface of the lower sheet containing a carbon coating. The top surface of the upper sheet contains a series of blocks wherein the student indicates his answer. The blocks are arranged so that all answers for a particular page of the test booklet are placed in a single column of the answer sheet. The top surface of the bottom sheet contains a carbon coating which transposes marks made on the top surface of the upper sheet to the backside of the upper sheet where a single box is located corresponding to the box representing the correct choice in the series of boxes placed on the opposite side. The grader or machine which scores the examination counts the blackened spaces. While this physical structure makes it easier for the grader to score the examination, the mode of testing is limited to multiple choice and true-false type questions, and the corrected answer sheet neither supplies a meaningful correct answer nor references a source of materials to remediate the student's deficiencies.

Accordingly, the physical structure of the present invention is an improvement over the art, because by placing the printed answer in proximity to the space where the student's response is recorded, the grader can immediately mark the examination without resort to an answer sheet or a key, and the student is supplied with a correct answer to the question without further effort by the instructor. The present invention contemplates the use of any of several modes of questioning, such as objective, short answer, true-false, or multiple choice responses. Because the examination can be rapidly graded and returned to the student with correct answers furnished thereon, the examination becomes a more effective teaching device. The value of the present invention is further enhanced by the use of prescriptions which are supplied on the scoring sheet itself. A series of prescriptions printed on the scoring sheet permits the teacher to select one as a source of further study for the student. Use of the prescriptions in conjunction with the rapid grading and corrected answer sheet supplies an effective teaching tool which is relatively inexpensive and which consumes relatively little of the instructor's time.

SUMMARY OF THE INVENTION

The invention may generally be described as a diagnostic skills test particularly adapted to be used as a teaching device. The diagnostic skills test consists of two sheets of paper oriented so that one overlies the other. Both sheets of paper are joined at the margins by a temporary binding which prevents visual inspection of the top surface of the second sheet by the student. The top surface of the first sheet contains interrogatories and spaces where the student may register his answers, the bottom surface of the top sheet contains a coating which causes the answer made on the top surface of the top sheet to be registered on the top surface of the second, underlying sheet. The top surface of the second sheet contains the correct answer proximate the location of the student's answer transposed thereon and also contains prescriptions whereby the teacher may indicate further sources of study for remediation.

DETAILED DESCRIPTION

Figure 1:
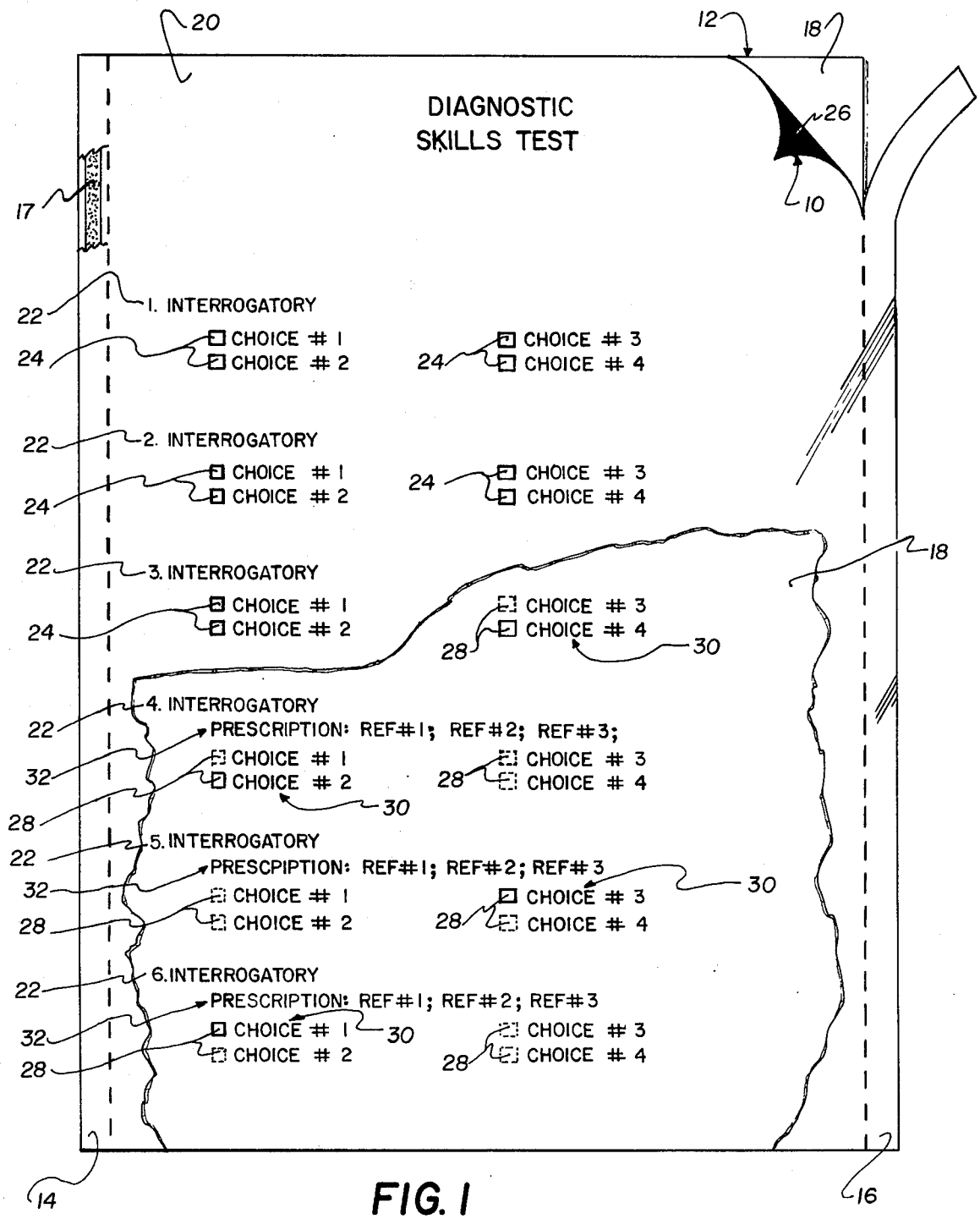
FIG. 1 schematically depicts a multiple choice examination in accordance with a first embodiment of the invention shown in plan view with portions broken away to illustrate underlying portions.
Figure 2:
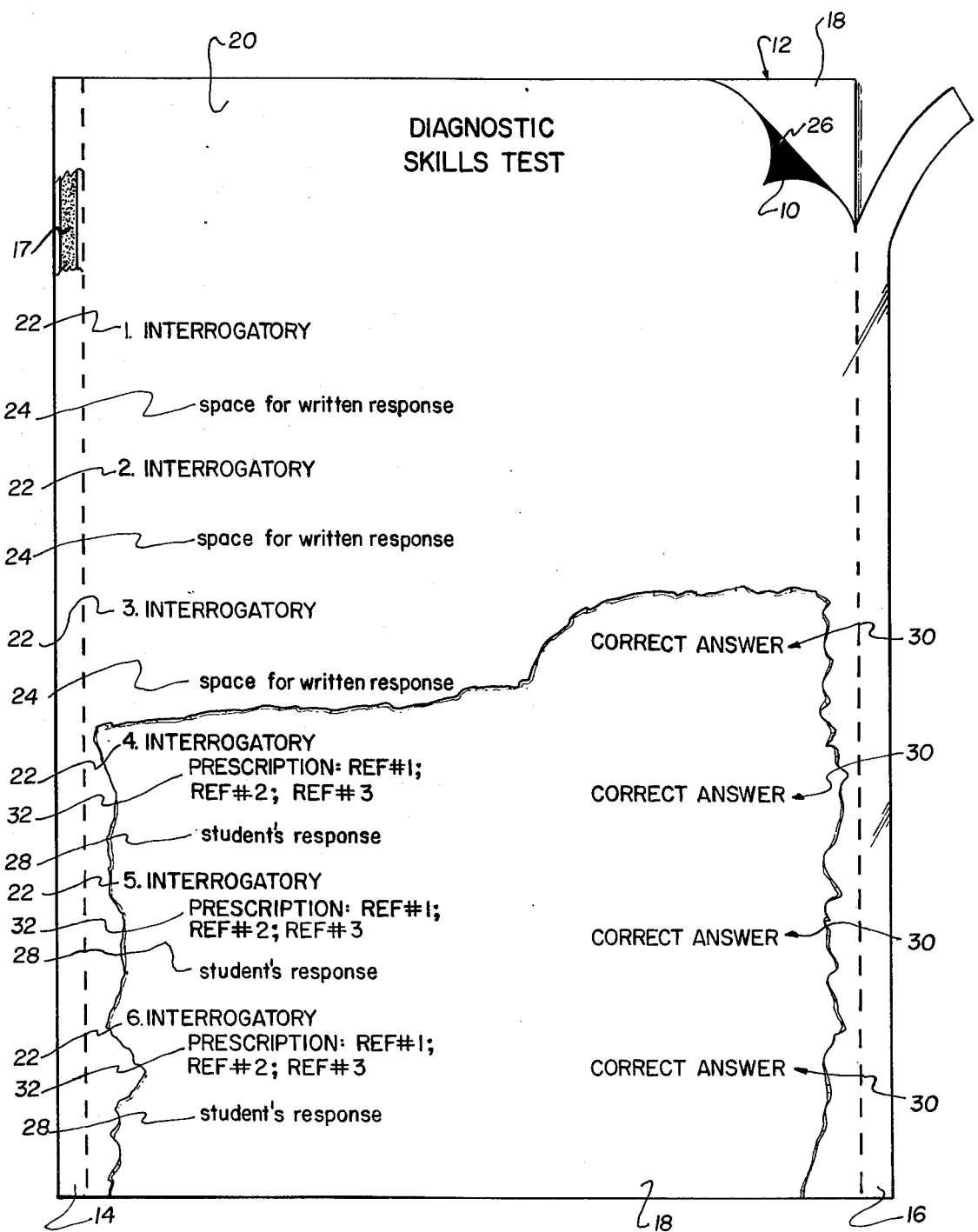
FIG. 2 schematically depicts a short answer examination in accordance with a second embodiment of the invention shown in plan view with portions broken away to illustrate underlying portions.

Now referring to the figures of the drawing, two exemplary embodiments of the inventive diagnostic test will be described, like numerals being used to designate similar elements in each embodiment.

The physical structure of the invention consists of two sheets of paper 10 and 12 oriented so that one sheet 10 overlies the other 12 and the margins 14 and 16 of the two sheets are bound together with a suitable adhesive 17 to prevent exposure of the top surface 18 of the second, underlying sheet 12 to the student's view. The top surface 20 of the upper sheet contains interrogatories 22 to be answered by the student. Adjacent the interrogatories 22 are predetermined spaces 24 in which the student registers his response to that question. The backside 26 of the top sheet 10 contains a coating of carbon or NCR paper, which by means of the pressure applied to the top surface 20 of the upper sheet 10, causes markings to register on the top surface 18 of the second, underlying sheet 12 in corresponding predetermined spaces 28 thereon.

In close proximity to the space 28 on the second sheet where the student's response to a particular interrogatory is transposed, is printed the correct answer 30. By juxtaposing the correct answer 30 with the student's response in the space 28, the grader can easily score the examination and with no additional effort provide the student with a corrected examination. The effectiveness of the corrected answer sheet 12 can be further enhanced by printing thereon, in reduced type, if necessary, the interrogatories 22 on the first sheet 10 so that the interrogatories 22, the student's answer and the correct answer 30 all appear on the same paper.

In proximity to the printed answer 30 and predetermined answer space 28 on the top surface 18 of the second sheet 12 are a series of written prescriptions 32 referencing sources of study to which the student may refer for further remediation. The grader may select a specific prescription tailored to the needs of that particular student as evidenced by the student's performance on the test and as personally known to the grader. The prescriptions 32 are set out in order of difficulty so that the grader may choose one which is appropriate for the needs and ability of the student.

This examination format is especially well adapted to reading or foreign language programs in which there is a library of materials for instructional and remedial purposes.

When the student taking the examination reads an interrogatory 22 and records his response in the predetermined space 24 adjacent thereto, the pressure exerted by the pencil or pen on the top surface 20 of the upper sheet 10 will cause a similar marking to be transposed onto the top surface 18 of the second sheet 12 by means of the carbon surface which coats the bottom surface 26 of the top sheet 10. When the examination is completed, the instructor collects the tests and separates the top portion 10 from the bottom portion 12 by tearing off the perforated bindings 14 and 16 in the indicated manner. The upper sheet 10 can be discarded, and the grader may then correct the examination paper by comparing the correct answer 30 with the student's response in the space 28 and then designate a prescription 32 when appropriate. Since the examination can be corrected with minimum effort, it can be timely returned to provide the student with a corrected examination paper which references sources of information to which he may turn to remedy his lack of knowledge or skills.

Although particular embodiments of the invention have been described herein, it will be understood that the invention is not limited to the embodiments disclosed, but is capable of rearrangement, modification and substitution of parts and elements without departing from the spirit of the invention.

What is claimed is:

1. A diagnostic test for students which facilitates determination of the student's present knowledge and identifies materials for additional study if the student has insufficient knowledge, which test comprises:

first and second sheets of paper, said second sheet disposed adjacent to and underlying said first sheet;

writing on the top surface of said first sheet posing interrogatories to be answered by the student;

predetermined spaces provided on the top surface of said first sheet for such answers, which predetermined spaces are in close proximity to the interrogatories;

a coating on the bottom surface of said first sheet, portions of said coating being transferrable to underlying portions of the top surface of said second sheet upon the application of pressure to corresponding portions of the top surface of said first sheet;

predetermined answer spaces on the top surface of said second sheet which register with corresponding predetermined answer spaces on the top surface of said first sheet, whereby a student responding to the interrogatories written on the top surface of said first sheet by selectively applying pressure to portions of said predetermined answer spaces on the top surface of said first sheet to indicate one or more answers will cause portions of the coating on the bottom surface of said first sheet to be transferred to portions of said predetermined answer spaces on the top surface of said second sheet;

indicia within or in close proximity to said predetermined answer spaces on the top surface of said second sheet which indicate the correct answers to the interrogatories contained on the top surface of the first sheet, whereby it can be determined whether the student's answers represented by said portions of transferred coating are correct or incorrect by comparison with said indicia;

writing on the top surface of said second sheet prescribing one or more source references of information which will supply remediation for incorrect responses to the interrogatories; and removable binding means for temporarily binding margins of said first and second sheets in abutment to prevent visual inspection of the top surface of said second sheet until said means are removed permitting separation of said paper sheets.

2. The test of claim 1 wherein said removable binding means is characterized in that at least the lateral margins of said first and second sheets are coextensive and are affixed to each other by an adhesive substance and said first and second sheets are perforated along lateral margins inwardly of the adhesive substance to permit the lateral margins to be removed and said first and second sheets separated.

3. The test of claim 1 wherein the writing on the top surface of said second sheet prescribing said one or more source references of information which will supply remediation provides a plurality of source references graduated according to difficulty, whereby the instructor can indicate any one or several of said source references appropriate for the needs and ability of the particular student.

4. The test of claim 1 wherein the top surface of said second sheet contains writing reproducing the same interrogatories as are posed on the top surface of said first sheet, said interrogatories on the top surface of said second sheet being disposed in proximity to the corresponding predetermined answer spaces thereon.

* * * * *